(12) United States Patent
Malinowski et al.

(10) Patent No.: US 10,094,843 B2
(45) Date of Patent: Oct. 9, 2018

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventors: Michal Malinowski, Backnang (DE); Achim Sinz, Waiblingen (DE); Florian Mueller, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/062,267

(22) Filed: Mar. 7, 2016

(65) Prior Publication Data

US 2016/0282378 A1    Sep. 29, 2016

(30) Foreign Application Priority Data

Mar. 23, 2015  (EP) .................................... 15160360

(51) Int. Cl.
| | |
|---|---|
| G01N 21/00 | (2006.01) |
| B01L 9/00 | (2006.01) |
| G01N 35/02 | (2006.01) |
| G01N 35/04 | (2006.01) |
| B60K 7/00 | (2006.01) |
| B65G 45/10 | (2006.01) |
| B65G 45/22 | (2006.01) |
| B65G 54/02 | (2006.01) |
| G01N 35/10 | (2006.01) |

(52) U.S. Cl.
CPC ......... *G01N 35/026* (2013.01); *B60K 7/0007* (2013.01); *B65G 45/10* (2013.01); *B65G 45/22* (2013.01); *B65G 54/02* (2013.01); *G01N 35/04* (2013.01); *G01N 35/1004* (2013.01); *G01N 2035/0475* (2013.01); *G01N 2035/0477* (2013.01); *G01N 2035/0489* (2013.01); *G01N 2035/0496* (2013.01)

(58) Field of Classification Search
USPC ............................................ 422/63, 65, 561
See application file for complete search history.

(56) References Cited

U.S. PATENT DOCUMENTS

| | | |
|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Dean Kwak
(74) *Attorney, Agent, or Firm* — Roche Diagnostics Operations, Inc.

(57) ABSTRACT

A laboratory sample distribution system comprising a transport plane and a cleaning device for cleaning the transport plane is presented. The cleaning device is adapted to automatically clean the transport plane similar to sample container carriers moving also on the transport plane. A laboratory automation system comprising such a laboratory sample distribution system is also presented.

5 Claims, 2 Drawing Sheets

(56) References Cited

U.S. PATENT DOCUMENTS

| | | |
|---|---|---|
| 4,771,237 A | 9/1988 | Daley |
| 5,120,506 A | 6/1992 | Saito et al. |
| 5,295,570 A | 3/1994 | Grechsch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mod et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1* | 8/2012 | Bleau .................. B65G 45/14 198/494 |
| 8,281,888 B2 | 10/2012 | Bergmann |
| 8,502,422 B2 | 8/2013 | Lykkegaard |
| 8,796,186 B2 | 8/2014 | Shirazi |
| 9,211,543 B2 | 12/2015 | Ohga et al. |
| 9,239,335 B2 | 1/2016 | Heise et al. |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1* | 10/2006 | Kelly .................. B65G 45/24 198/495 |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0236445 A1* | 9/2010 | King .................. B60L 13/003 104/130.03 |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0090734 A1* | 4/2014 | Kusko .................. F16K 31/1245 137/624.27 |
| 2014/0170023 A1 | 6/2014 | Saito |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2014/0263429 A1* | 9/2014 | Keating .................. B67D 3/0003 222/54 |
| 2015/0014125 A1 | 1/2015 | Hecht |
| 2015/0082754 A1* | 3/2015 | Jasiulek .................. B65B 43/52 53/473 |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1* | 10/2015 | Pollack .................. G01N 35/00623 348/143 |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1* | 3/2017 | Riether .................. G01N 35/026 |
| 2017/0096307 A1 | 4/2017 | Mahmudimanesh et al. |
| 2017/0097372 A1 | 4/2017 | Heise et al. |
| 2017/0101277 A1* | 4/2017 | Malinowski .................. B65G 54/02 |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1* | 5/2017 | Volz .................. G01N 35/04 |
| 2017/0138971 A1 | 5/2017 | Heise et al. |

(56) References Cited

U.S. PATENT DOCUMENTS

| | | |
|---|---|---|
| 2017/0160299 A1 | 6/2017 | Schneider et al. |
| 2017/0168079 A1* | 6/2017 | Sinz ................ G01N 35/04 |
| 2017/0174448 A1* | 6/2017 | Sinz ................ B65G 54/02 |
| 2017/0184622 A1* | 6/2017 | Sinz ............ G01N 35/00693 |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A * | 4/1986 ............ B65G 54/02 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | 63-031918 * | 2/1988 |
| JP | S63-31918 A | 2/1988 |
| JP | S63-48169 | 2/1988 |
| JP | S63-82433 U | 5/1988 |
| JP | S63-290101 A | 11/1988 |
| JP | 01-148966 A | 6/1989 |
| JP | H01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-026808 A | 4/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 A | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013152089 A1 | 10/2013 |
| WO | 2013/169778 A1 | 11/2013 |
| WO | 2013177163 A1 | 11/2013 |
| WO | 2014/059134 A1 | 4/2014 |
| WO | 2014071214 A1 | 5/2014 |

* cited by examiner

US 10,094,843 B2

LABORATORY SAMPLE DISTRIBUTION SYSTEM AND LABORATORY AUTOMATION SYSTEM

CROSS-REFERENCE TO RELATED APPLICATIONS

This application claims priority to EP 15160360.2, filed Mar. 23, 2015, which is hereby incorporated by reference.

BACKGROUND

The present disclosure relates to a laboratory sample distribution system and to a laboratory automation system comprising such a laboratory sample distribution system.

Laboratory sample distribution systems can be used in order to distribute samples between a plurality of laboratory stations in a laboratory automation system. For example, a two-dimensional laboratory sample distribution system providing high throughput is known in the art. Electro-magnetic actuators are disposed below a transport plane in order to drive sample container carriers carrying sample containers on the transport plane.

It has been observed in known laboratory sample distribution systems that a transport plane on which a plurality of sample container carriers move is subject to contamination, both due to dust and due to a possible spilling over of samples. Such contamination can lead to decreased system performance and can even pose the risk of contaminating the samples, which could lead to wrong analyzing results.

Therefore, there is a need for a laboratory sample distribution system and a laboratory automation system comprising such a laboratory sample distribution system in which contamination of the transport plane can be accounted for.

SUMMARY

According to the present disclosure, a laboratory sample distribution system and a laboratory automation system comprising such a laboratory sample distribution system are presented. The laboratory sample distribution system can comprise a plurality of sample container carriers adapted to carry one or more sample containers; a cleaning device; a transport plane adapted to support the sample container carriers and the cleaning device; a driver adapted to move the sample container carriers and the cleaning device on top of the transport plane; and a control device configured to control the movement of the sample container carriers and to control the movement of the cleaning device on top of the transport plane by driving the driver such that the sample container carriers move along corresponding transport paths and that the cleaning device moves along a cleaning path. The cleaning device comprises a cleaner adapted for cleaning the transport plane.

Accordingly, it is a feature of the embodiments of the present disclosure to provide a laboratory sample distribution system and a laboratory automation system comprising such a laboratory sample distribution system in which contamination of the transport plane can be accounted for. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
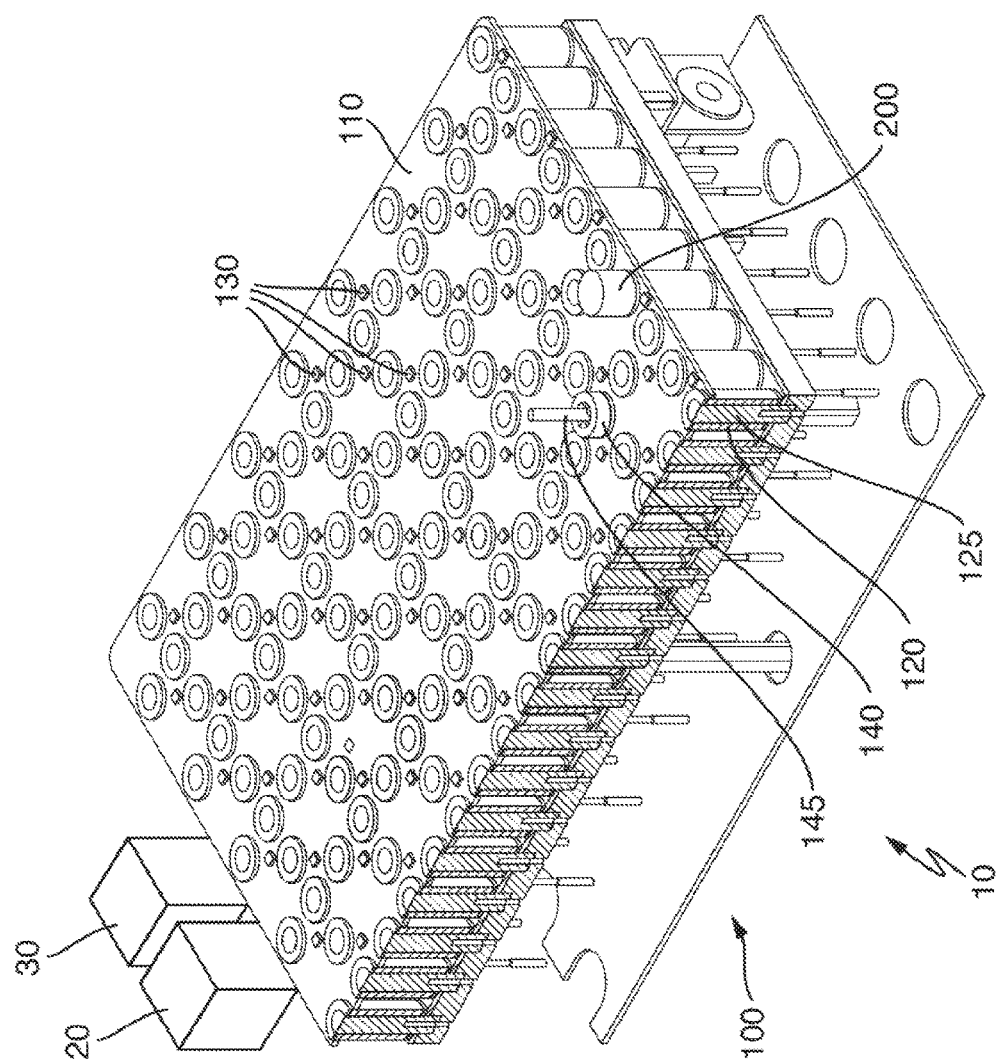
FIG. 1 illustrates a laboratory automation system comprising a laboratory sample distribution according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented. The laboratory sample distribution system can comprise a plurality of sample container carriers adapted to carry one or more sample containers. It can comprise a cleaning device. It can further comprise a transport plane adapted to support the sample container carriers and the cleaning device.

The laboratory sample distribution system can comprise a driver adapted to move a sample container carrier and the cleaning device on top of the transport plane in two dimensions (x- and y-dimension). It can further comprise a control device configured to control the movement of the sample container carriers and to control the movement of the cleaning device on top of the transport plane by driving the driver such that the sample container carriers can move along corresponding transport paths and that the cleaning device can move along a cleaning path. The cleaning device can comprise a cleaner adapted for cleaning the transport plane.

By using the inventive laboratory sample distribution system, the functionality of a laboratory sample distribution system can be enhanced by a cleaning device that is adapted to clean the transport plane. Dust, spilled over samples or other contamination on the transport plane can be automatically removed by the cleaning device. The cleaning device can be controlled by the control device so that no manual action is required in order to clean the transport plane. There is also no need to stop operation of the laboratory sample distribution system in order to clean the transport plane. The cleaning device can move similar to the sample container carriers during normal operation. The cleaning device can be driven over the transport plane such that a continuous cleaning of the complete transport plane can be provided.

According to one embodiment, the cleaner can comprise a cleaning cloth. Such a cleaning cloth can easily gather dust or other contamination on the transport plane. The cleaning cloth can be an antistatic cleaning cloth. Such an implementation can help to reduce electrostatic charge that can arise due to friction of the cleaning cloth on the transport plane.

According to one embodiment, the cleaning cloth can be a microfiber cleaning cloth. Such microfiber cleaning cloths can have a high capacity regarding gathering of dust or other substances on the transport plane.

According to one embodiment, the cleaning device can comprise a container for storing a cleaning fluid and a disposer for disposing the cleaning fluid over the transport plane. Such a cleaning fluid can be helpful in cleaning the transport plane. For example, it can contain substances that can help remove contaminants from the transport plane and to take them away by a cleaning cloth. For example, it can contain water, which can contain cleaning agents. The cleaning fluid can also contain agents for chemical deactivation or decomposition of potentially hazardous substances.

According to one embodiment, the cleaning device can comprise electrostatic discharger adapted to discharge the transport plane or parts of the transport plane. Such a discharger can, for example, have an electrical connection to a ground potential in order to remove electrostatic charges that can arise on the transport plane due to friction of the sample container carries on the transport plane.

According to one embodiment, the control device can be configured to control movement of the sample container carriers and the cleaning device such that the sample container carriers can have priority over the cleaning device. This can allow for an uninterrupted operation of the laboratory sample distribution system such that throughput and fast transport of samples may not be disturbed by the operation of the cleaning device. For example, the control device may be configured to stop the cleaning device if a sample container carrier crosses its intended cleaning path.

According to one embodiment, the control device can be configured to activate a cleaning function of the cleaning device, especially to activate disposing of a cleaning fluid. For example, such an activation can be performed if the control device is aware of a specific contamination on the transport plane. For example, such a contamination can be detected by a camera connected to the control device, or it can be inputted manually by an operator viewing the contamination.

According to one embodiment, the cleaning device and the sample container carriers can have identical horizontal cross-sections and/or outline. This can reduce complexity in the operation of the laboratory sample distribution system because the cleaning device and the sample container carriers can be handled with identical algorithms regarding their space requirements on the transport plane. For example, an algorithm for collision avoidance may not have to distinguish between a cleaning device and a sample container carrier.

According to one embodiment, the driver can be formed as electro-magnetic actuators located below the transport plane and controllable by the control device. The electro-magnetic actuators can be arranged in rows and columns below the transport plane. The sample container carriers and the cleaning device can each comprise a magnetically active device for interaction with a magnetic field generated by the electro-magnetic actuators such that a magnetic drive force can be applied to the sample container carriers and to the cleaning device. The magnetically active device can be embodied as a permanent magnet.

According to one embodiment, the driver can be formed as wheels driven by electric motors located in the sample container carriers and in the cleaning device and controllable by the electronic control device.

The embodiments with the driver being electro-magnetic actuators or wheels, respectively, can represent implementations of a laboratory sample distribution system that can be suitable for typical applications.

It can be noted that a laboratory sample distribution system can also comprise a plurality of cleaning devices as just described.

A laboratory automation system is also presented. The laboratory automation system can comprise a plurality of laboratory stations such as, for example, pre-analytical, analytical and/or post-analytical stations. It can further comprise an inventive laboratory sample distribution system.

Regarding the laboratory sample distribution system, all embodiments, implementations and variations as discussed herein can be applied. With the laboratory automation system, the advantages discussed above with respect to a laboratory sample distribution system can be applied for a laboratory automation system.

The laboratory stations may be arranged adjacent to the laboratory sample distribution system. The laboratory sample distribution system may be adapted to transport the sample container carriers and/or sample containers between the laboratory stations.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exists.

Post-analytical stations may be adapted to perform any kind of post-processing of samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

Referring initially to FIG. 1, FIG. 1 shows a laboratory automation system 10. The laboratory automation system 10 can comprise a first analytical station 20, a second analytical station 30 and a laboratory sample distribution system 100. The first and second laboratory stations 20, 30 are shown here only exemplarily, wherein it is to be understood that a typical laboratory automation system can comprise more than two laboratory stations in order to perform certain tasks like analyzing, recapping or aliquoting of samples or sample containers.

The laboratory sample distribution system 100 can comprise a transport plane 110. Below the transport plane 110, a plurality of electro-magnetic actuators 120 can be arranged. Each electro-magnetic actuator 120 can comprise a ferromagnetic core 125. The electro-magnetic actuators 120 can be embodied as solenoids.

A plurality of position sensors 130, which can be embodied as Hall-sensors, can be distributed over the transport plane 110.

On the transport plane 110, there can be arranged a sample container carrier 140 carrying a sample container 145. The sample container carrier 140 can comprise a magnetically active device embodied as a permanent magnet, which is not visible in FIG. 1 because it is located inside the sample container carrier 140. A magnetic field generated by the permanent magnet of the sample container carrier 140 can interact with magnetic fields generated by the electro-magnetic actuators 120 such that a drive force can be applied to the sample container carrier 140.

The laboratory sample distribution system 100 can further comprise a control device 150. The control device can be adapted to control the electro-magnetic actuators 120. Thus, the control device 150 can control the magnetic fields generated by the electro-magnetic actuators 120 and can thus control movement of the sample container carrier 140. The control device 150 can be adapted to move the sample container carrier 140 over the transport plane 110 using the electro-magnetic actuators 120 along a transport path. For example, the sample container 145 can be brought to and from the laboratory stations 20, 30. The position of the sample container carrier 140 can be monitored by the position sensors 130, which can also be connected to the control device 150.

It can be understood that a typical laboratory sample distribution system 100 can comprise more than one sample container carrier 140. The single sample container carrier 140 is only shown exemplarily, wherein typical laboratory sample distribution systems can comprise a plurality of such sample container carriers in order to achieve a high throughput.

The laboratory sample distribution system 100 can further comprise a cleaning device 200. The cleaning device 200 can be embodied with a horizontal cross-section identical to the horizontal cross-section of the sample container carrier 140. The cleaning device 200 can be used to clean the transport plane 110. Further details of the cleaning device 200 will be explained below with reference to FIG. 2.

Figure 2:
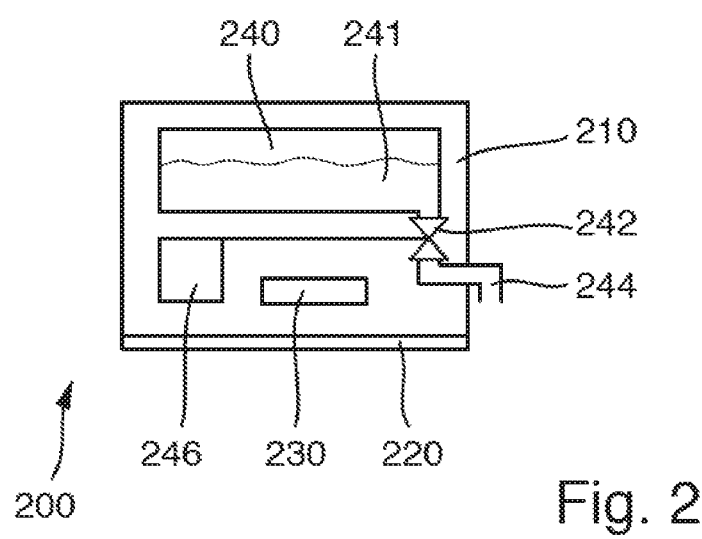
FIG. 2 illustrates a cross-sectional view of a cleaning device of the laboratory automation system shown in FIG. 1 according to an embodiment of the present disclosure.

FIG. 2 shows a schematic cross section of the cleaning device 200 of FIG. 1. The cleaning device 200 can comprise a main body 210 and a cleaner embodied as a cleaning cloth 220. The cleaning cloth 220 can be a microfiber cleaning cloth and can have antistatic properties. The cleaning cloth 220 can be adapted to be the element of the cleaning device 200 that comes into contact with the transport plane 110 when the cleaning device 200 moves over the transport plane 110. By use of the cleaning cloth 220, the cleaning device 200 can collect dust or other contamination that may be present on the transport plane 110.

The cleaning device 200 can further comprise a magnetically active device embodied as a permanent magnet 230. The permanent magnet 230 can generate a magnetic field that can interact with magnetic fields generated by the electro-magnetic actuators 120. Thus, the cleaning device 200 can be moved over the transport plane 110 in the same way as the sample container carrier 140. It can be noted that the control device 150 can be configured to control movement of the cleaning device 200 similar to the sample container carrier 140, wherein sample container carriers 140 can generally have priority over the cleaning device 200.

The cleaning device 200 can further comprise a container 240 that can store a cleaning fluid 241. The cleaning fluid 241 can basically comprise water in which a cleaning agent can be dispersed. Below the container 240, a valve 242 can be arranged. The valve 242 can be connected with the container 240 and with an outlet opening 244 that can be located outside the main body 210. The valve 242 can be connected with a receiver 246. The receiver 246 can be adapted to receive signals by wireless transmission from the control device 150. Thus, the control device 150 can trigger the valve 242 to dispose the cleaning fluid 241 on the transport plane 110. This can support cleaning of the transport plane 110 by the cleaning device 200. The valve 242, the outlet opening 244 and the receiver 246 can thus be called a disposer, because it can be adapted to dispose the cleaning fluid 241 on the transport plane 110 when required.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising:
   a plurality of sample container carriers configured to carry one or more sample containers;
   a control device;
   a cleaning device, wherein the cleaning device comprises a container for storing cleaning fluid and a valve arranged below the container, wherein the valve is connected to the container and an outlet opening, wherein the valve comprises a receiver in wireless communication with the control device to receive signals from the control device to open or close the valve, and wherein the control device sends a signal to the receiver to open the valve and dispose cleaning fluid;
   a transport surface configured to support the sample container carriers and the cleaning device, wherein the cleaning device comprises a cleaner configured for cleaning the transport surface; and
   a driver configured to move the sample container carriers and the cleaning device on top of the transport surface, wherein the driver comprises electromagnetic actuators located below the transport surface, and wherein the sample container carriers and the cleaning device each comprise a magnetically active device for interaction with a magnetic field generated by the electromagnetic actuators such that a magnetic drive force is applied to the sample container carriers and the cleaning device;
   the control device is configured to control the movement of the sample container carriers and to control the movement of the cleaning device on top of the transport surface by activating the electromagnetic actuators of driving the driver to generate the magnetic drive force such that the sample container carriers move along corresponding transport paths and that the cleaning device moves along a cleaning path, and such that the transport paths of the sample container carriers have priority over the transport path of the cleaning device.

2. The laboratory sample distribution system according to claim 1, wherein the cleaner comprise a cleaning cloth.

3. The laboratory sample distribution system according to claim 2, wherein the cleaning cloth is a microfiber cleaning cloth.

4. The laboratory sample distribution system according to claim 1, wherein the cleaning device comprises a container for storing a cleaning fluid and a disposer for disposing the cleaning fluid over the transport surface.

5. The laboratory sample distribution system according to claim 1, wherein the cleaning device and the sample container carriers have identical horizontal cross sections.

* * * * *